United States Patent [19]

Shimizu et al.

[11] 4,024,073
[45] May 17, 1977

[54] HYDROGEL AND PRODUCTION THEREOF

[75] Inventors: Hirohiko Shimizu; Hitoshi Ozawa, both of Kamakura, Japan

[73] Assignee: Toray Industries, Inc., Tokyo, Japan

[22] Filed: Feb. 21, 1975

[21] Appl. No.: 551,669

Related U.S. Application Data

[63] Continuation of Ser. No. 314,811, Dec. 13, 1972, abandoned.

[30] Foreign Application Priority Data

Jan. 8, 1972 Japan .................................. 47-4795

[52] U.S. Cl. ............................... 252/316; 106/186; 106/194; 536/18; 536/22
[51] Int. Cl.² ........................ B01J 13/00; C08L 3/02
[58] Field of Search ............... 424/19, 35; 106/186, 106/194, 197, 213, 197 C; 252/316; 260/231 CM

[56] References Cited

UNITED STATES PATENTS

| | | | |
|---|---|---|---|
| 3,378,070 | 4/1968 | Wessler | 106/194 |
| 3,804,174 | 4/1974 | Chatterjl | 106/194 |

OTHER PUBLICATIONS

59:5385C, Chem. Abstracts.

*Primary Examiner*—Theodore Morris

[57] ABSTRACT

A novel and stable hydrogel contains a water-soluble polymer containing a chelating agent bound to the polymer chain, and a polyvalent metal ion cross-linking the polymer molecules through the chelating agent. The hydrogel is a carrier for timed release of drugs and medicaments.

7 Claims, No Drawings

HYDROGEL AND PRODUCTION THEREOF

This is a continuation of application Ser. No. 314,811, filed Dec. 13, 1972, now abandoned.

DESCRIPTION OF THE PRIOR ART

It is known that some hydrogels may be synthesized and used as carriers for sustained-release medicaments and insoluble enzymes for instance. As references, see for example Analytical Chemistry, 38 726 (1966), and G. P. Hicks and S. J. Updike U.S. Pat. No. 3,279,996. However, these known hydrogels are not well suited for practical use because of their instability, toxicity, etc.

SUMMARY OF THE INVENTION

This invention relates to a novel stable, elastic, non-toxic and biodegradable hydrogel for use as a carrier for sustained-release medicaments such as insulin, as a carrier for electro-phoresis, as a carrier for insoluble enzymes and as an adduct for foods.

An object of this invention is to provide a novel hydrogel having good stability and elasticity.

Another object of this invention is to provide a stable, elastic, non-toxic and biodegradable hydrogel, especially suited for use as a carrier for sustained-release medicaments.

A still further object of this invention is to provide a process for producing said hydrogel.

The above and other objects of this invention will be apparent from the following description.

DESCRIPTION OF THE PREFERRED EMBODIMENTS

The hydrogel according to this invention comprises a water-soluble polymer containing a chelating agent (or ligand residue) bound to a polymer chain and a metal ion having a valence of 2 or above (polyvalent), in which polymers are cross-linked through chelation between two chelating agents (or ligand residues) by the polyvalent metal ion.

The backbone polymer of this invention is selected from well known water-soluble polymers, preferably those which are non-toxic and biodegradable. Polysaccharides and polypeptides with chelating residues are remarkably effective as water-soluble polymers in the practice of this invention.

Typical examples of polysaccharides according to this invention include dextrans such as dextran, carboxymethyl dextran, diethylaminoethyl dextran, aminoethyl dextran and dextran sulfate, starches such as soluble starch, amylose, carboxymethyl amylose, hydroxyethyl amylose, hydroxypropyl amylose, carboxymethyl starch, cellulose such as carboxymethyl cellulose and hydroxyethyl cellulose, agarose, pectic acid, alginic acid, gum Arabic, galactomannan, Levan, hyaluronic acid and so on.

Typical examples of polypeptides which are useful according to this invention include polyglutamic acid, polylysine, proteins such as gelatin, casein and albumin, and so on.

The preferred molecular weight of the water-soluble polymer is about 10,000 – 1,000,000.

According to this invention the water-soluble polymer is converted to a polymer having a chelating residue which is bound to the polymer chain, by any suitable manner known in the art.

The chelating residues which are bound to the backbone polymers are those which can form a chelate with two or more chelating residues and one metal ion, thus resulting in cross-linking between the polymers by virtue of the chelate bonding. In addition to the chelate forming functional groups, the chelating molecules must have another functional group through which the chelating entities are bound to the polymer chain. Such chelating compounds include $\alpha$-amino acids with functional side chains, such as glutamic acid, lysine, ornitine, aspertic acid, cystine, histidine, tyrosine and p-aminophenylalanine, $\alpha$, $\omega$-diaminodicarboxylic acids such as diaminopimelic acid, iminodiacetic acid and its derivatives, anthranylic acid and its derivatives, salicylic acid and its derivatives and diethylenetriamine are preferable. There are many methods for combining the chelating compound with the polymer chain. Typical examples of such chelate-introducing reactions are as follows.

| Side chain of polymer | Functional group of chelating agent | Linkage to be given |
|---|---|---|
| - COOH | - OH | - COO - |
|  | - $NH_2$ | - CONH - |
| - $NH_2$ | - COOH | - CONH |
| - OH | - COOH | - COO - |
|  | - halogen | - O - |
|  | - $NH_2$ | - OCONH - |
|  |  | - $CH_2$ - NH - |

The chelate-introducing reaction may be carried out in a manner and under conditions which are well known in the art; they include the so-called "Peptide syntheses."

Typical known methods which are available for use as the chelate-introducing reaction are described in the following publications:

R. Axen, J. Porath, and S. Ernback, Nature, 214 1302 (1967);
J. Porath, R. Axen, S. Ernback, Nature 215 1491 (1967);
M. A. Mitz, L. J. Summaria, Nature, 189 576 (1961);
F. Mitchell, J. Evans, Macromolecular Chemse, 3 200 (1949);
N. Grubhofler, L. Schleith, Naturwissenschaften, 40 508 (1953);
D. G. Hoare, D. E. Koshland, J. American Chemical Society 88 2057 (1966);
M. A. Mitz, L. J. Summalia, Nature, 189 576 (1961);
R. Axen, J. Porath, Acta Chemica Scandinavia, 18 2193 (1964);
R. Axen, J. Porath, Nature 210 367 (1966).

In the chelate-introducing reaction, chelating agents are introduced preferably in a quantity of about 1 – 100 moles per every hundred monomer units in the polymer, more preferably about 2 – 20 moles per hundred monomer units.

In accordance with this invention the water-soluble polymer with the chelate residue, produced as above, is contacted with metal ions having a valence of 2 or above in an aqueous solution, in order to produce the hydrogel.

Any of these polyvalent metal ions capable of coordinating with two or more chelating agents may be used.

Typical examples of the metal ions are transition metal ions such as $Cu^{2+}$, $Cr^{3+}$, $Fe^{2+}$, $Fe^{3+}$, $Co^{2+}$, $Ni^{2+}$ and $Zn^{2+}$, alkali earth metal ions such as $Mg^{2+}$ and $Ca^{2+}$, and $Al^{3+}$. The metal ion may be added as a water-soluble salt of an organic or inorganic acid such as hydrochloric, hydrobromic, sulfuric, acetic, maleic and phthalic acid, for example.

Gelation may be carried out by contacting an aqueous solution of the polymer plus chelating residue, in which concentration is preferably 1 to 70% by weight, with the metal ion solution at a temperature from about room temperature to about 100° C.

The suitable amount of the metal ion to be used may vary considerably but is preferably about 0.1 to 10 equivalents, more preferably about 0.1 to 0.5 equivalent, per equivalent of chelating agent. Gelation takes place preferably at a pH of about 3 to 10.

If necessary, an adjustment of pH is carried out by adding a base such as caustic soda, ammonia or trialkylamine, or by dialysis.

Although gelation can be effected easily at room temperature, heating accelerates gelation.

A suitable temperature for gelation, when heating is desired, is about 40° to about 80° C.

The hydrogel produced as above comprises a water-soluble-polymer containing the chelating agent bound to the polymer chain and polyvalent metal ions, in which the polymers are cross-linked through chelation between two chelating agents through metal ions, and in which preferably about 1 to 100 moles, more preferably 2 to 20 moles, of chelating agents and preferably about 0.5 to 50 moles, more preferably about 1 to 10 moles, of metal ions per every hundred monomer units of the polymer are present. The water content of the hydrogel is preferably about 50 to 99% by weight, more preferably about 70 to 95% by weight based on the total weight of the hydrogel.

In the case of cystine-containing polymer, the hydrogel can be formed by treating the polymer solution with a trace amount of thiol compound at a slightly alkaline pH. A disulfide exchange reaction occurs and the whole mass becomes a hydrogel in which the polymer chains are cross-linked.

Hydrogels in accordance with this invention are particularly useful when combined with certain medicaments or drugs, which are entrapped in the hydrogel and have the characteristic of sustained release. Drug action is sometimes transient and the effect upon the patient sometimes disappears more rapidly than desired after its administration. For example, when insulin is injected into the patient, the blood sugar level drops almost immediately but comes back substantially to its original level within about 8 hours. To overcome this disadvantage, various efforts have heretofore been made. For example, the addition of zinc ion, together with regulating the size of the zinc-insulin crystal (Lente- or Ultra-Lente-insulin), and administration of a mixture of zinc-insulin and protamine have been found to extend the period of effectiveness of the insulin. These approaches are mainly dependent on the basic idea of reducing the solubility of the drug, and consequently have severe limitations when used to prolong the action of the drug.

The hydrogel of this invention has been found to have many advantages in that it is very effective both for the prolongation and control of the effective action of the drug.

Thus, a sol solution of the water-soluble polymer with the chelating residue is mixed with a solution of insulin or other selected drug having a molecular weight over 3000, and the mixture thus prepared is brought to the hydrogel form by simply adding the metal ion.

The hydrogel, which contains the entrapped insulin or other drug within its gel matrix, can be homogenized and injected either subcutaneously or intramuscularly.

The release rate of the entrapped drug can be regulated primarily by controlling the pore size of the gel. The pore sizes of hydrogels, as clearly understood in the field of gel-chromatography, are determined by the water content of the gel.

A practical embodiment is, for example, about 1 – 70 wt.% aqueous solution of the water-soluble polymer with a chelating agent and a concentrated solution of a high molecular weight drug, which are mixed well and to which a polyvalent metal ion is added, and the pH of the solution is adjusted to a range where the chelation is most favorable. Thus, a hydrogel with about 0.1 – 10 wt.% of said drug and about 1 – 50 wt.% of the polymer is obtained.

The drug to be entrapped within the hydrogel must have a molecular weight of more than about 3000, otherwise the drug cannot be entrapped effectively within the hydrogel. Typical useful drugs include several kinds of hormones, such as insulin, ACTH, and thyroglobulin; some polyanions which have an interferon inducing activity, for example, a double stranded complex of polyinosinic and polycytidylic acid, double stranded viral RNA, and some enzymes of practical value, such as urease, catalase, uricase, glucose isomerase and asparaginase.

In the last case, the enzyme need not be released from the hydrogel so long as the substrate and the products are small enough to pass into and diffuse out of the hydrogel with reasonable speed.

The hydrogel-drug can be used in various ways, such as by injection, implant, oral administration, suppository or surgical use.

The following examples are illustrative of the invention:

EXAMPLE 1

To an aqueous solution of 10 gm of Dextran T-150 (Pharmacia, Uppsala, Sweden) in 2 liters of de-ionized water was added 100 ml of an aqueous solution of 5 gm of cyanogen bromide. The reaction mixture was kept at pH 11.0 for 7 min. at room temperature by careful dropwise addition of 5N-NaOH. Several hundred grams of cracked ice were added immediately to lower the temperature of the reaction mixture below 5° C and the activated dextran was allowed to couple with 185 mmoles of cystine in 200 ml of an aqueous solution, pH 10.2, containing 0.2 mmole of ethylenediaminetetra-acetate at pH 10 overnight in the cold room. The excess cystine was filtered off after precipitation by neutralizing the reaction mixture with 6N-HCl. The filtrate was evaporated to a volume of about 300 ml under reduced pressure and dialyzed thoroughly against de-ionized water after solubilizing the cystine which was precipitated during evaporation by raising the pH of the mixture to 10.5 with 5N-NaOH. Lyophilization of the dialyzed solution yielded 11 gm of cystinedextran T-150 in which cystine is covalently bound to dextran through either of the two α-amino groups.

The amount of bound cystine was 0.303 μmole per mg of the product when analyzed as cysteic acid in an amino acid autoanalyzer after performic acid oxidation, that is 4.9 molecules of cystine are bound per every 100 glucose residues in the polysaccharide backbone.

The cystine-dextran preparation thus obtained is still water-soluble and can form a hydrosol of higher than 30 wt.% polymer concentration. The hydrosol was capable of transformation to a transparent and elastic hydrogel under conditions suitable to cross-link the polymer chains intermolecularly, either by chelation with polyvalent metal ions or by disulfide bridges formed by a disulfide exchange reaction. For example, to the hydrosol of 1 – 70 wt.% of the polymer concentration was added a concentrated aqueous solution of metal ion in an amount of 0.1 – 10 molar ratio of metal ion to cystine and, after being mixed well, the pH of the mixture was adjusted to such a pH as the intermolecular chelate bridge could be formed, generally pH 4 – 10 or more preferably pH 7.5 – 9, by direct addition of an aqueous solution of a base such as NaOH, $NH_4OH$ or triethylamine, and mixed well. Though gelation proceeded even at room temperature, heat accelerated the gelation process so markedly that the whole mass became a homogeneous and elastic hydrogel in 5 min. to several hours by heating the above mixture to 40° – 80° C, the water content of which is 50 – 99 wt.%. Several kinds of metal salts were used for the purpose, such as chloride, nitrate, phosphate, sulphate, acetate, formate, fumarate, lactate, malate, maleate, phthalate, succinate, and other salts of metal ions such as magnesium, aluminum, calcium, chromic, manganese, ferrous, ferric, cobaltous, nickel, cupric and zinc ions, though among these salts such salts as chloride, acetate, maleate and phthalate are usually recommended because of their ease of handling and gelation. Because the hydrogel system depends primarily on the formation of an interchain chelate bridge through a metal ion at an appropriate pH, some modifications of the method of gelation are acceptable; for example, metal ions can be supplied through a semipermeable membrane by dialyzing a hydrosol of the polymer packed in a cellophane casing against an aqueous solution of metal ions or, by the same principle, the pH of a hydrosol of the polymer containing metal ions can be adjusted by dialyzing against a suitable buffer solution when it is necessary to prevent the formation of metal hydroxides which was observed occasionally on the direct addition of alkali or a hydrosol of the polymer containing metal ions was spread on a glass plate as a film and contacted with ammonia vapor to bring the pH of the hydrosol to alkalinity and an elastic thin film of the hydrogel was obtained. Another method of gelation of the cystine polymer is the formation of interchain disulfide bridges by a disulfide exchange reaction. A hydrosol of 20 wt.% of cystine-dextran was adjusted to pH 8.5 – 9 and heated at 80° C for 1 hour to form a transparent and elastic hydrogel. Because thiol compounds such as 2-mercaptoethanol, cysteine and dithiothreitol accelerate disulfide exchange reaction markedly, a 10 wt.% hydrosol of cystine-dextran could be transformed to a hydrogel without heating by standing overnight at room temperature in the presence of 0.01 – 1 equivalent of 2-mercaptoethanol to cystine at pH 9.

Several polymers such as soluble starch, amylose, hydroxyethylamylose, hydroxypropylamylose, carboxymethylamylose, carboxymethylstarch and carboxymethylcellulose could be coupled with cystine by the same method as described above, except that carboxymethylcellulose was marcelized overnight in a cold room in 400 ml of 17.5% NaOH under a nitrogen atmosphere prior to the reaction, and also such polymers as amylose, amylose derivatives and carboxymethylstarch were marcelized in 1N-NaOH for several hours to overnight in the cold room, to obtain a high yield of cystine coupling. Sol-gel transformation as described above was observed with all cystine polymers synthesized and the results are summarized in the table which follows Example 3.

The hydrogels of the cystine polymers were solubilized by several methods, such as specific enzymatic digestion of the polymer backbone by enzymes such as dextranase, amylase and cellulase, or reduction with a large excess of a thiol compound such as 2-mercaptoethanol and cysteine, or such treatments as incubation with hydroxylamine or heating under extremely acidic or alkaline conditions to split the bond between cystine and the polymer.

EXAMPLE 2

To a solution of 1 gm of cystine-dextran which was obtained as in Example 1, in 20 ml of de-ionized water was added 18.3 gm of 2-mercaptoethanol and the product was allowed to stand overnight at pH 8.5 under a nitrogen atmosphere to reduce the cystine molecules. After acidification to pH 4 with glacial acetic acid, the mixture was dialyzed thoroughly against 0.1 M-acetic acid and lyophilized to yield 0.70 gm of cysteine-dextran. The thiol group content of the product was 0.10 $\mu$mole/mg.

A hydrosol of 10 wt.% of cysteine-dextran was adjusted to pH 8.5 and air-oxidized overnight at room temperature to form a transparent and elastic hydrogel by interchain disulfide

EXAMPLE 3

Dextran T-150, carboxymethylstarch, and carboxymethylcellulose were coupled with a copper complex of lysine (Cu:Lys = 1:2) instead of cystine by the same method in principle as described in Example 1. In this case the reaction mixture was dialyzed thoroughly against 0.01 N-HCl to ensure the decomposition of the copperlysine complex and to prevent ionic binding of lysine to polyanionic polymer. The lysine content of the product was determined by amino acid analysis. The lysine-dextran contained 3 - 8 moles of lysine per 100 glucose residues and the lysine carboxymethylstarch contained about 5 moles of lysine per 100 glucose units and the lysine carboxymethylcellulose contained about 2 moles of lysine per 100 glucose residues.

Because lysine is bound covalently to the polymer through its $\epsilon$-amino group, addition of metal ions causes the formation of an interchain chelate bridge. Thus, hydrogels of lysine polymers were obtained by chelation as described in Example 1. The results are shown in the following table.

The hydrogels of the lysine polymer were solubilized by an enzymatic digestion or by removing metal ions on mild heating in the presence of enough ethylenediaminetetraacetate which is a stronger chelator than lysine.

Table 1
PREPARATION AND DEGREE OF SWELLING OF HYDROGELS

| Polymer | Ligand (mol/100 res) | Concentration (wt. %) | Metal/ligand | | Condition of Gelatin treatment | Degree of Swelling* |
|---|---|---|---|---|---|---|
| Dextran T-150 | lysine 7.7 | 16.7 | $Co^{++}$ | 1/1 | pH 8.5, dialyzed 2 days | 7.2 |
| | | 16.7 | $Co^{++}$ | 1/2 | pH 8, 60° C, 15 hr. | 4.6 |
| | | 16.7 | $Mg^{++}$ | 1/2 | pH 8, 60° C, 15 hr. | > 12 |
| | | 16.7 | $Fe^{+++}$ | 1/2 | pH 8, 60° C, 15 hr. | > 27 |
| | cystine 4.9 | 16.7 | $Co^{++}$ | 10/3 | pH 8.5, dialyzed 2 days | 3.8 |
| | | 16.7 | $Zn^{++}$ | 1/1 | pH 6, 80° C, 1 hr. | 5.4 |
| | | 16.7 | $Co^{++}$ | 1/1 | pH 8, 80° C, 1 hr. | 10 |
| | | 16.7 | $Ni^{++}$ | 1/1 | pH 4, 80° C, 1 hr. | 5.6 |
| | | 16.7 | $Mn^{++}$ | 1/1 | pH 8, 80° C, 1 hr. | 7.8 |
| | | 16.7 | $Fe^{++}$ | 1/1 | pH 7, 80° C, 1 hr. | 8.7 |
| | | 16.7 | $Al^{+++}$ | 1/1 | pH 11, 80° C, 1 hr. | 3.9 |
| Carboxymethyl- | lysine 1.8 | 18.9 | $Co^{++}$ | 1/1 | pH 8, 80° C, 1 hr. | 2.7 |
| cellulose 1140 (DS 0.7) | cystine 1.7 | 9.1 | $Mg^{++}$ | 10/1 | pH 8, 80° C, 1 hr. | 9.8 |
| | | 9.1 | $Mg^{++}$ | 1/1 | pH 8, 80° C, 1 hr. | 17 |
| Carboxymethyl- | cystine 1.1 | 1.0 | $Zn^{++}$ | 5/1 | pH 8, 80° C, 1 hr. | > 15 |
| cellulose 1190 (DS 0.7) | | 4.8 | $Zn^{++}$ | 5/1 | pH 8, 80° C, 1 hr. | 7.9 |
| | | 11.1 | $Zn^{++}$ | 5/1 | pH 8, 80° C, 1 hr. | 3.5 |
| Poly-glutamate (DP 630) | lysine 7.4 | 16.7 | $Co^{++}$ | 1/2 | pH 8, 80° C, 1 hr. | 17 |
| Carboxymethyl- | lysine 5.1 | 16.7 | $Co^{++}$ | 1/1 | pH 8, 80° C, 1 hr. | 4.5 |
| starch (DS 0.30) | cystine 3.8 | 16.7 | $Al^{++}$ | 1/1 | pH 8, 80° C, 1 hr. | 9.0 |
| Soluble starch | cystine 7.5 | 33.3 | $Ca^{++}$ | 1/4 | pH 8, 80° C, 1 hr. | 4.1 |
| Amylose | cystine 4.6 | 16.7 | $Zn^{++}$ | 1/2 | pH 8, 60° C, 2 hr. | 10 |
| | | 16.7 | $Zn^{++}$ | 1/1 | pH 8, 60° C, 2 hr. | 3.6 |
| | | 16.7 | $Zn^{++}$ | 2/1 | pH 8, 60° C, 2 hr. | 1.8 |
| | | 16.7 | $Ca^{++}$ | 1/2 | pH 8, 60° C, 2 hr. | 3.7 |
| | | 16.7 | $Ca^{++}$ | 2/1 | pH 8, 60° C, 2 hr. | 4.2 |
| | | 16.7 | $Ca^{++}$ | 8/1 | pH 8, 60° C, 2 hr. | 3.7 |
| Carboxymethyl-amylose (DS 0.50) | cystine 3.1 | 16.7 | $Zn^{++}$ | 2/1 | pH 8, 60° C, 2 hr. | 43 |
| Hydroxyethyl-amylose (DS 0.15) | cystine 4.9 | 36.3 | $Mg^{++}$ | 1/2 | pH 8, 80° C, 1 hr. | 3.4 |
| Hydroxypropyl-amylose (DS 0.35) | cystine 8.3 | 20.0 | $Zn^{++}$ | 1/4 | pH 8, 60° C, 2 hr. | 2.8 |
| | | 20.0 | $Zn^{++}$ | 1/1 | pH 8, 60° C, 2 hr. | 2.1 |
| | | 20.0 | $Zn^{++}$ | 4/1 | pH 8, 60° C, 2 hr. | 1.4 |

*Hydrogel blocks (0.2 – 1.0 gm) were swollen in water for 3 – 12 days with several exchanges of water until they reached constant weights and weight ratio of final to intial were determined.

EXAMPLE 4

Five gm of sodium salt of poly-L-glutamic acid (degree of polymerization, 630) was dissolved in 1l of de-ionized water and the solution was acidified to pH 2 by the addition of 6N HCl. The poly-L-glutamic acid thus precipitated was centrifuged, washed with water, and dissolved in 100 ml of pyridine. After adding 6.8 g of dicyclohexylcarbodiimide and stirring for ten minutes, a copper complex of lysine containing 75.6 mmoles of lysine was added. The reaction was caused to proceed overnight with stirring. Ethylenediamine tetraacetate was added and the reaction mixture was allowed to stand for several hours. Insoluble material was centrifuged off and the supernatant solution was dialyzed toward water and then 0.1 N hydro-chloric acid. On lyophilization, 3.5 g of reaction product which contained 5.1 lysine residues per hundred glutamic acid residues was obtained.

A gel was prepared when cobalt ion was added to the sol solution, as described in Example 1.

EXAMPLE 5

Poly-L-glutamic acid obtained as described in Example 4 was lyophilized and stored in a vacuum desiccator over $P_2O_5$.

Acetic anhydride (3.3 mmoles) was added to a solution of dried poly-L-glutamic acid while the pH was maintained at 8.8 with occasional addition of triethylamine.

To the solution of N-acetyl-poly-L-glutamic acid thus obtained was added dioxane saturated with hydrogen chloride gas until the pH of the solution became 6.0. To this were added 13.5 mmoles of p-nitrophenyl trifluoroacetate and the reaction mixture was stirred overnight at room temperature.

The remaining p-nitrophenyl trifluoroacetate was decomposed by adding 10 ml of water, and 13.5 m moles of triethylamine was added to neutralize the trifluoroacetic acid that was formed. A solution of copper complex of lysine (0.135 moles of lysine in 270 ml $H_2O$) was added and the pH was kept at 8.5 with triethylamine. After two days' coupling reaction, hydrochloric acid (6N) was added until the pH was 1.5, and the precipitate was centrifuged.

The precipitate was dialyzed well toward 0.01 N HCl and lyophylized, giving 2.28 g of N-acetyl-poly-L-glutamic acid-Lysine. The polymer contained 6.6 lysine residues per hundred glutamic acid residues.

An equivalent amount of cobaltous chloride to lysine was added to a 20% solution of the polymer at pH 9.0, and when the solution was heated at 60° for a while, a pale pink colored transparent and elastic gel was obtained. When the coupling reaction was carried out with cystine, p-amino-salicylic acid or diethylene triamine instead of lysine, N-acetyl-poly-L-glutamic acid with each chelating group were obtained. The amount of chelating molecule are hundred glutamic acid residues were:

|  | Chelating groups/100 G |
|---|---|
| P-ASA | 5.0 |
| DETA | 6.5 |
| Cys | 1.3 |

The polymer formed gels by the same procedures as described above.

EXAMPLE 6

N-Chloroacetyl-lysine had been synthesised by reacting chloroacetylchloride with copper-complex of lysine. The N-chloroacetyl-lysine (40 mmoles) was dissolved in 10 ml of water and added to a solution of dextran T-150 (10 g in 30 ml of 10 N NaOH). The reaction was carried out at 70° for 20 minutes. The reaction mixture was neutralized and dialyzed well against water. On lyophylization it gave 9.5 g of carboxymethyldextran-lysine, of which the lysine content was 5.6 moles per hundred glutamic acid residues. Thus, the polymer can form a gel by the same procedures as described in Example 4.

EXAMPLE 7

To an ice-chilled solution of 10 g of soluble starch in 100 ml of 0.2M acetate buffer, pH 4, 3.21 g of sodium metaperiodate in 50 ml of an aqueous solution was added and the reaction mixture was allowed to stand for 15 minutes in the dark. To destroy unreacted periodate 0.84 ml of ethyleneglycol was added and left for a further 30 minutes, then the pH of the mixture was brought to 10 with 5N-NaOH. A 50 ml aqueous solution containing 30 mmoles of cystine and 1 mmole of disodium ethylenediaminetetra-acetate, pH 10.2, was added and stirred overnight in the cold room. While ice-cooling, 56 gm of sodium borohydride was added to the reaction mixture with careful portionwise additions not to elevate the temperature and the reduction proceeded for 3 days in the cold room under argon. The reaction mixture was acidified to pH 2 with 6N-HCl and allowed to stand for 30 minutes at room temperature to decompose the unreacted sodium borohydride. To the mixture were added 60 moles of cysteine and after raising the pH to 9 the mixture was air-oxidized for three days at room temperature with bubbling. The insoluble mass was filtered off and the filtrate was dialyzed thoroughly against to water and lyophilized to yield 8.5 gm of cystine-soluble starch. The product contained 0.26 mmole of cystine per gram.

An elastic hydrogel was obtained as described in Example 4.

EXAMPLE 8

A solution of insulin (19.5 mg of insulin in 0.61 ml of 0.01 N-HCl) was added to 200 mg of carboxymethylamylosecystine (degree of carboxymethylation 0.5 mol/100 glucose residue) and mixed well. To this, 0.16 ml of 1 M-CoCl$_2$ was added and the pH of the mixture was adjusted to 7.0 – 8.5 with careful addition of 5 N-NaOH. The mixture was heated at 60° for 3 hours to accelerate the gelation.

The gel thus obtained was homogenized in Potter-Elvehjem's homogenizer with 10 ml of 0.9% sodium chloride solution.

The resulting suspension was centrifuged and the amount of insulin in the supernatant solution was analyzed. The gel was extracted repeatedly with fresh physiological saline solution and analyzed for insulin. The results are summarized below.

| (After homogenizing 0 hr. | 2 hrs. | 1 day | 2 days | 5 days | 7 days | Total eluted | Remained in Gel | Total Recovery |
|---|---|---|---|---|---|---|---|---|
| 4.7% | 6.2% | 7.6% | 4.9% | 5.4% | 4.5% | 35.6% | 50.1% | 85.7% |

EXAMPLE 9

A solution of insulin (150 mg in 3.0 ml of 0.01 N-HCl) was added to 1.80g of carboxymethylamylosecystine (degree of carboxymethylation 0.2 mol/glucose residue, cystine 7.2 mol/100glucose residues) and mixed well. Zinc chloride solution (1.0 M, 0.4 ml) and sodium hydroxide was added to bring the pH to 7.0 and heated at 60° C for 2 hours. The gel thus obtained was homogenized with 40 ml of physiological saline solution.

The homogenate contained 80.0 IU insulin per ml of the homogenate. The homogenate was injected into alloxan diabetes rabbits in an amount of 25 IU/kg, 50 IU/kg, 75 IU/kg, 100 IU/kg, respectively. The blood sugar was measured from time to time. The results are summarized below.

|  | 0 hr. | 3 hrs. | 8 hrs. | 1 day | 2 days | 3 days | 4 days | 5 days |
|---|---|---|---|---|---|---|---|---|
| 25 IU/kg | 100% | 20 | 44 | 38 | 74 | 82 | 90 | 90 |
| 50 IU/kg | 100% | 28 | 43 | 57 | 37 | 68 | 81 | 99 |
| 75 IU/kg | 100% | 22 | 52 | 53 | 36 | 35 | 44 | 55 |
| 100 IU/kg | 100% | 15 | 22 | 33 | 23 | 55 | 28 | 49 |

-continued

|  | 6 days | 7 days | 8 days | 9 days | 10 days | 11 days | 13 days | 15 days | 17 days |
|---|---|---|---|---|---|---|---|---|---|
| 25 IU/kg | 111 | 91 | 92 | 102 | 93 |  | 101 | 96 |  |
| 50 IU/kg | 102 | 86 | 84 | 96 | 111 |  | 112 | 77 |  |
| 75 IU/kg | 60 | 77 | 89 | 93 | 95 |  | 95 | 94 |  |
| 100 IU/kg | 41 | 39 | 27 | 43 | 53 | 69 | 113 | 101 | 103 |

EXAMPLE 10

Hog Kidney acylase (11.3 mg = 207 U) was dissolved in 0.4 ml of 0.2 M malete buffer. Three hundred mg of Dextran-cystine (cystine 6.3 moles per hundred glucose residues) was added and mixed well, and subsequently 120 μmoles of cobaltous chloride and 1 N sodium hydroxide was added.

The gel was kept at 31° C overnight. A part of the gel containing 10.5 mg = 200 U acylase was homogenized with 10 ml of 0.01 M maleate buffer at pH 6.5. The whole homogenate showed 145 U of acylase activity (73%).

The gel had swollen during the homogenation, and the polymer concentration of the gel at this stage was 13%. No further swelling was observed thereafter. All the activity was associated with the gel and there appeared to be no activity in the supernatant fraction.

The gel was extracted with 10 ml each of the buffer solution 5 times, but (almost apparently) no enzymatic activity could be detected in the supernatant fractions (the sum up of the five extractions is 3 U).

The gel was finally hydrolyzed with 6 N-HCl and the acylase content was found to be 10.2 mg (97.3%) from the results of amino acid analysis of the hydrolyzate, thus showing that the entrapment of the enzyme was complete.

The acylase activity of the gel after final extraction was 67 U, 46% of the original. When the acylase solution with the concentration as in the gel was stored at 4° – 5° C for 5 days, similar inactivation (48% of the original) was observed, showing that entrapment of the acylase in the hydrogel does not prevent or accelerate the inactivation.

The following is claimed:

1. A hydrogel comprising a water-soluble polymer selected from the group consisting of dextrans, starches and celluloses containing a chelating agent selected from the group consisting of cystine and lysine bound to the polymer chain and a polyvalent metal ion, in which the polymers are cross-linked through chelation between the chelating agents by said polyvalent metal ion.

2. A hydrogel of claim 1 in which the said water-soluble polymer contains about 1 to 100 of said chelating agent per one hundred monomer units in the polymer.

3. A hydrogel of claim 1 in which the polyvalent metal ion is selected from the group consisting of the alkali earth metals, transition metals, and aluminium ions.

4. A method for preparing a hydrogel which comprises contacting an aqueous solution of a water-soluble polymer selected from the group consisting of dextrans, starches and celluloses containing a chelating agent selected from the group consisting of cystine and lysine bound to a polymer chain, in which the concentration of the polymer is about 1 to 70% by weight, with a polyvalent metal ion at a temperature from about room temperature to about 100° C.

5. A method of claim 4 in which gelation is carried out by dialysis.

6. A hydrogel comprising carboxy methyl amylose bound to cystine and a zinc ion, wherein said carboxy methyl amylose is cross-linked through chelation between said cystine and said zinc ion.

7. A hydrogel comprising a water-soluble starch containing a chelating agent selected from the group consisting of cystine and lysine bound to said starch and a polyvalent metal ion, in which said starch is cross-linked through chelation between the chelating agents by said polyvalent metal ion.

* * * * *